(12) United States Patent
Cimino

(10) Patent No.: US 6,391,042 B1
(45) Date of Patent: *May 21, 2002

(54) PULSED ULTRASONIC DEVICE AND METHOD

(75) Inventor: William W. Cimino, Louisville, CO (US)

(73) Assignee: Sound Surgical Technologies LLC, Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/476,879

(22) Filed: Jan. 4, 2000

Related U.S. Application Data

(63) Continuation of application No. 09/260,297, filed on Mar. 2, 1999, now Pat. No. 6,027,515.

(51) Int. Cl.$^7$ ............................................. A61B 17/32
(52) U.S. Cl. ............................................. 606/169; 604/22
(58) Field of Search ................................. 606/169, 167, 606/185; 604/21, 22; 601/1, 2

(56) References Cited

U.S. PATENT DOCUMENTS

| | | |
|---|---|---|
| 3,673,475 A | 6/1972 | Britton |
| 3,980,906 A | 9/1976 | Kuris |
| 4,343,111 A | 8/1982 | Inoue |
| 4,614,178 A | 9/1986 | Harit |
| 4,827,911 A | 5/1989 | Broadwin |
| 5,808,398 A * | 9/1998 | Boukhny ..................... 604/22 |
| 5,976,167 A * | 11/1999 | Lee ............................. 606/169 |

OTHER PUBLICATIONS

Analog Devices 1992 Special Linear Reference Manual application notes for AD633. pp. 2–52;53.

* cited by examiner

*Primary Examiner*—Kevin Truong
(74) *Attorney, Agent, or Firm*—Merchant & Gould, P.C.

(57) ABSTRACT

This invention relates generally to ultrasonic surgical apparatus. More particularly, this invention relates to an improved method and apparatus for generating profiled pulses of ultrasonic frequency vibratory energy at a distal surface of an ultrasonic applicator of an ultrasonic surgical instrument for application to tissues of a patient with specific relationships between a magnitude of the pulse of ultrasonic frequency vibratory energy and a duration of the pulse of ultrasonic frequency vibratory energy so that the ultrasonic applicator can be driven to vibratory amplitudes previously not achievable and a more expedient surgical effect obtained.

6 Claims, 3 Drawing Sheets

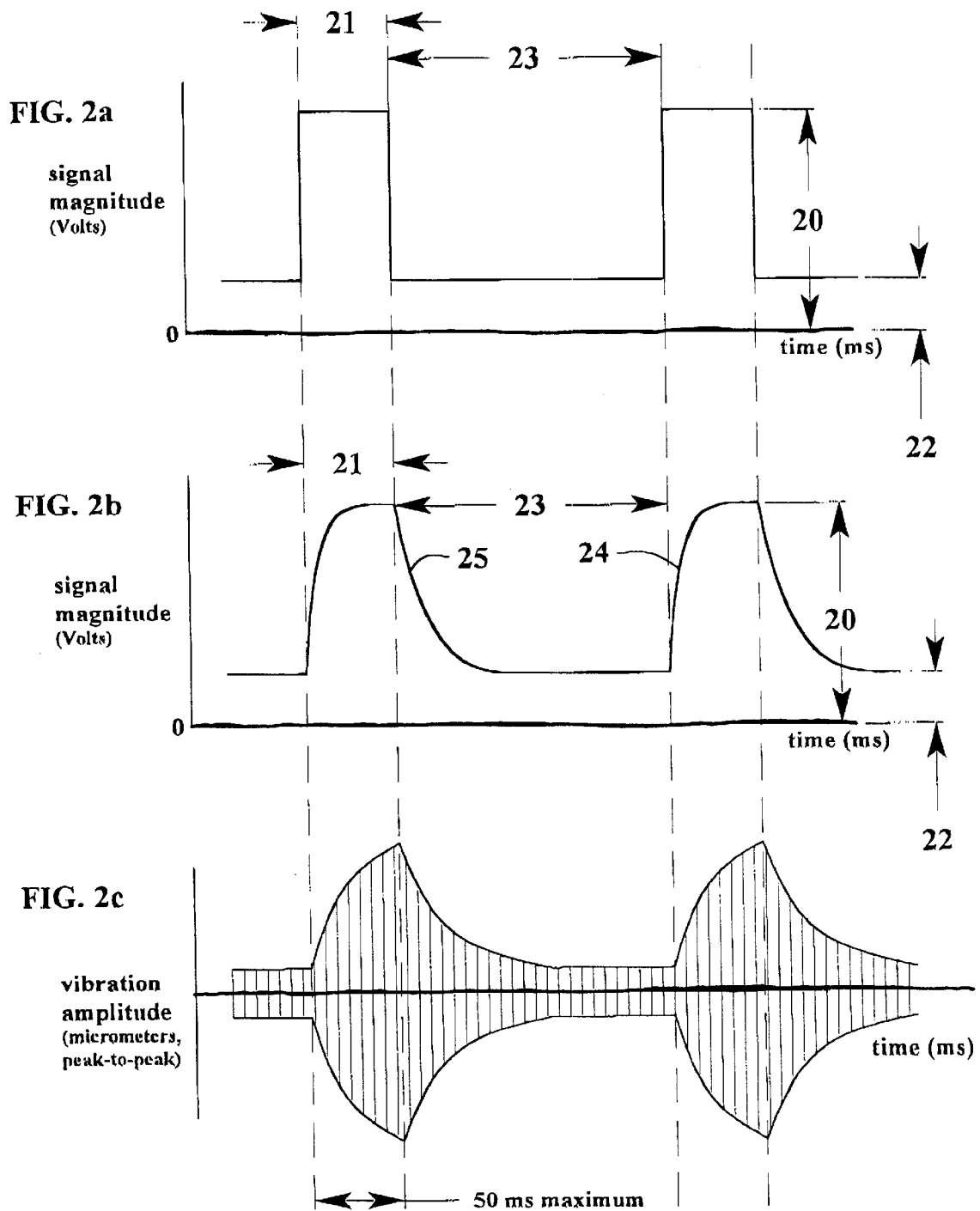

PULSED ULTRASONIC DEVICE AND METHOD

PATENT

CROSS-REFERENCE TO RELATED APPLICATION

This application is a continuation of and claims priority to U.S. application Ser. No. 09/260,297, which was filed Mar. 2, 1999 now U.S. Pat. No. 6,027,515.

SPECIFICATION

Background of the Invention

This invention relates generally to ultrasonic surgical apparatus. More particularly, this invention relates to an improved method and apparatus for generating profiled pulses of ultrasonic frequency vibratory energy at a distal surface of an ultrasonic applicator of an ultrasonic surgical instrument for application to tissues of a patient with specific relationships between a magnitude of the pulse of ultrasonic frequency vibratory energy and a duration of the pulse of ultrasonic frequency vibratory energy so that the ultrasonic applicator can be driven to vibratory amplitudes previously not achievable and a more expedient surgical effect obtained.

Ultrasonic surgical devices typically operate at frequencies between 20 kHz and 60 kHz and have application in many surgical specialties including neurosurgery, general surgery, and ophthalmic surgery. In general it is known that ultrasonic surgical devices generate ultrasonic frequency vibratory energy that is applied to an ultrasonic applicator that vibrates longitudinally and which contacts the tissues of a patient. The ultrasonic surgical device may, among other surgical effects, cut, fragment, and/or coagulate the contacted tissues of the patient.

Ultrasonic surgical devices are constrained in their ability to generate ultrasonic frequency vibratory energy due to limits imposed by machining tolerances and by limits inherent in the physical characteristics of the materials used to fabricate the devices. For example, titanium alloys are often used for fabrication of the ultrasonic applicator that is used to contact the tissues of a patient. Titanium alloys have inherent fatigue strength and stress limitations that cannot be exceeded or the ultrasonic applicator will crack. As a further example, the ultrasonic motor that converts supplied electrical power to ultrasonic frequency vibratory energy may be fabricated from piezoelectric ceramics. Piezoelectric ceramics have inherent limitations on their ability to efficiently convert electrical energy to vibratory energy, including limits on applied voltage so that the ceramic elements do not loose their piezoelectric properties.

However, a phenomenon referred to in this disclosure as 'mode coupling', is most often responsible for establishing the upper performance bound of an ultrasonic surgical device. Mode coupling occurs when the vibratory amplitude of an ultrasonic applicator of an ultrasonic surgical device is increased to such a level that the ultrasonic frequency vibratory energy at the desired resonant frequency is coupled to other modes of vibration, referred to herein as 'parasitic modes'. The parasitic modes of vibration may be at lower frequencies, near-by frequencies, or higher frequencies, depending of the design of the system. The parasitic modes of vibration may be longitudinal modes or they may be transverse modes, or they may be more complicated coupled modes. Mode coupling is especially troublesome when the ultrasonic applicator is an elongate probe or catheter with a length greater than one wavelength at the resonant frequency of the particular ultrasonic surgical device. Mode coupling may occur for ultrasonic applicators shorter than one wavelength and may also occur for ultrasonic applicators that are not shaped like an elongate probe, for example, flat or convex radiating surfaces.

The most common type of mode coupling encountered for ultrasonic surgical devices is the stimulation of a lower or near-by frequency transverse mode so that the ultrasonic applicator vibrates in the desired longitudinal vibratory mode and an undesired transverse vibratory mode simultaneously. This type of coupled vibration can easily cause stresses in the ultrasonic applicator material sufficient to break the ultrasonic applicator.

Ultrasonic surgical devices that operate at high vibratory amplitudes also generate undesirable heat, primarily in the ultrasonic motor, but also in the material of the ultrasonic applicator due to internal friction and other losses as the ultrasonic applicator vibrates. If the ultrasonic motor becomes too hot during a typical procedure then active cooling, such as forced air or water cooling, of the ultrasonic motor is required, making the ultrasonic surgical handpiece more expensive and more cumbersome due to the additional supply lines. If the ultrasonic applicator becomes hot then the tissues of a patient may be unnecessarily burned.

Mode coupling and heat generation have placed fundamental limits on the performance of ultrasonic surgical systems. What has been discovered, and is disclosed herein, is an ultrasonic surgical apparatus and method for generating profiled pulses of ultrasonic frequency vibratory energy such that mode coupling is suppressed or eliminated so that the ultrasonic applicator can be driven to desired vibratory amplitudes which were previously unobtainable, thus increasing the expediency of a surgical procedure. Further, because the expediency of the surgical procedure is increased, the effective dose of ultrasonic frequency vibratory energy delivered to the tissues of a patient is minimized. Still further, because the ultrasonic applicator is driven to high vibratory amplitudes for only short periods of time, internal heating of the ultrasonic applicator is reduced, as is the electrical power consumed by the ultrasonic motor.

The use of switchable or pulsed vibratable tools is disclosed in patents. U.S. Pat. No. 4,614,178 to Harlt has a dose meter and a control circuit for switching the mode of operation in an ultrasonic therapeutic apparatus. A detector circuit is used to monitor the output to a treatment head so that a time measurement of the duration of the treatment can be switched between an enabled or disabled state. This therapeutic, not surgical, device is intended to deliver heat to the tissues of a patient and the switch between states of operation is used to ensure that a proper dose of heat is delivered to the patient.

U.S. Pat. No. 3,980,906 to Kuris has a driving circuit for producing bursts of ultrasonic frequency oscillations between 10 kHz and 1,000 kHz at repeated sonic intervals in the range of 10 Hz to 1,000 Hz, the repeated sonic intervals of ultrasonic frequency oscillation applied to ultrasonic instruments such as toothbrushes and razors. This patent uses bursts of ultrasonic energy to reduce sliding friction for smoother motion when shaving and to provide a satisfactory tactile sense of operation to a user. Each burst of ultrasonic mechanical vibration lasts for ½ of the sonic interval, resulting in on-off intervals of equal duration.

U.S. Pat. No. 4,343,111 to Inoue has an ultrasonic machining method wherein the vibratory energy is intermittently interrupted to create a series of time-spaced bursts of vibratory oscillation and the frequency or amplitude of the vibration is modified during each of the bursts. This patent uses of bursts of ultrasonic energy to reduce surface roughness of machined metal parts and to machine irregular contours into metal pieces.

U.S. Pat. No. 3,673,475 to Britton has a drive circuit for generating pulses that are applied to a dental impact tool with a reciprocating armature. This patent discloses a drive circuit to generate pulses to 'pull-back' and then 'drive' an armature, a technique that is not applicable to ultrasonic frequency vibratable tools.

None of the aforementioned patents teaches the use of profiled pulses of ultrasonic frequency vibratory energy for a surgical effect on tissues of a patient, none addresses using profiled pulses of ultrasonic frequency vibratory energy to suppress or eliminate the phenomenon described herein as mode coupling, and none suggests using profiled pulses of ultrasonic frequency vibratory energy to minimize internal heating in the ultrasonic applicator and the ultrasonic motor. The patents do not disclose any benefits due to relationships between the magnitude of the pulses of ultrasonic frequency vibratory energy and the duration of the pulses of ultrasonic frequency vibratory energy.

U.S. Pat. No. 4,827,911 to Broadwin has an ultrasonic surgical handpiece with a switching means for automatically and repeatedly switching the amplitude of ultrasonic vibration between a constant working high amplitude and a constant standby low amplitude, both used in combination with aspiration and irrigation, for enhanced fragmentation and improved surgical control. The invention works by interrupting continuous vibratory operation with on-off duty cycles, with suitable on-times for first, second, third, and fourth modes given as 50 milliseconds, 100 milliseconds, 150 milliseconds, and 200 milliseconds, respectively. The continuous vibratory operation is interrupted with a repetition rate of at least 30 Hz so that the operator does not distractedly sense the operation at low amplitude.

The Broadwin patent does not address or appreciate using profiled pulses of ultrasonic frequency vibratory energy to suppress or eliminate the phenomenon described herein as mode coupling, it does not address using profiled pulses of ultrasonic frequency vibratory energy to reduce heating in the ultrasonic applicator and the ultrasonic motor, nor does it disclose any benefits due to relationships between the magnitude of the pulses of ultrasonic frequency vibratory energy and the duration of the pulses of ultrasonic frequency vibratory energy.

OBJECTS OF THE INVENTION

It is, among other desirable attributes, an overall object of the present invention to provide a method and apparatus for delivering profiled pulses of ultrasonic frequency vibratory energy to an ultrasonic applicator for application to tissues of a patient with specific durations and magnitudes so that the ultrasonic applicator can be driven to vibratory amplitudes previously not achievable, and for a more expedient surgical effect to be obtained.

It is a further object of the present invention to provide a method and apparatus for delivering profiled pulses of ultrasonic frequency vibratory energy to an ultrasonic applicator for application to tissues of a patient with specific durations and magnitudes so that the phenomenon described herein as mode coupling is reduced, minimized, suppressed, or eliminated.

It is a still further object of the present invention to provide a method and apparatus for delivering profiled pulses of ultrasonic frequency vibratory energy to an ultrasonic applicator for application to tissues of a patient with specific durations and magnitudes so that a more expedient surgical effect is obtained, and therefore, the effective dose of ultrasonic frequency vibratory energy applied to the tissues of a patient is minimized.

It is yet still a further object of the present invention to provide a method and apparatus for delivering profiled pulses of ultrasonic frequency vibratory energy to an ultrasonic applicator for application to tissues of a patient with specific durations and magnitudes so that the electrical power consumed by the ultrasonic motor is minimized, resulting is a cooler running ultrasonic motor.

It is a final object of the present invention to provide a method and apparatus for delivering profiled pulses of ultrasonic frequency vibratory energy to an ultrasonic applicator for application to tissues of a patient with specific durations and magnitudes so that internal heating of the ultrasonic applicator is minimized.

SUMMARY OF THE INVENTION

The apparatus and method disclosed herein are directed toward achieving the aforementioned objects of the present invention. It has been learned through experimentation that previous switching between a constant high vibratory amplitude and a constant low vibratory amplitude results in mode coupling and the stimulation of parasitic modes of vibration, fundamentally limiting the efficient performance of those systems. It has been discovered that if a first time portion of a pulse ultrasonic frequency vibratory energy is preferably profiled as described herein and kept below an upper limit of about fifty milliseconds, and a second time portion of the pulse of ultrasonic frequency vibratory energy that follows the first time portion that is at least 3 times the time duration of the first time portion while the maximum vibratory amplitude is at least twice but not more than twenty times the minimum vibratory amplitude, then the mode coupling phenomenon can be suppressed or eliminated, thus allowing for operation at vibratory amplitudes previously not achievable. Thus, it is not how long the ultrasonic frequency vibratory energy is delivered, but the combination of the magnitude of the pulse of ultrasonic frequency vibratory energy and the duration and shape of the pulse of ultrasonic frequency vibratory energy that eliminates mode coupling, expedites a surgical procedure, minimizes the effective dose of ultrasonic energy to a patient, and minimizes heat generation in the ultrasonic motor and the ultrasonic applicator.

While the exact reason for successful operation with profiled pulses of ultrasonic frequency vibratory energy is not completely understood, the results obtained unequivocally demonstrate the objects of this invention. It is believed, in particular, that mode coupling is suppressed using this technique because there is insufficient time at the highest vibratory amplitudes to initiate vibration in and couple vibratory energy to parasitic modes of vibration. Further, it is believed that the previously unobtainable maximum vibratory amplitudes more efficiently and more effectively generate a surgical effect in the tissues of a patient, thus minimizing the effective dose of ultrasonic frequency vibratory energy required to complete a surgical procedure. If the first time portion of the pulse of ultrasonic frequency vibratory energy is less than about one millisecond mode coupling is suppressed but very little surgical effect is obtained. Therefore, in general, as the first time portion of the pulse of ultrasonic frequency vibratory energy is shortened, an increased maximum magnitude of vibration is required to achieve and maintain an expedient surgical effect. The repetitive duty-cycle systems of prior patents failed to appreciate or recognize the relationship between the magnitude and duration of pulses of ultrasonic frequency vibratory energy to achieve and maintain an effective and expedient surgical effect while eliminating problems due to mode coupling.

In general an ultrasonic surgical apparatus for delivery of profiled pulses ultrasonic frequency vibratory energy includes a housing to be held and manipulated by a user, an ultrasonic motor supported within the housing, and an ultrasonic applicator connected to the ultrasonic motor and extending beyond the housing. Piezoelectric ceramics such as PZT-4 or PZT-8 are the preferred materials for the ultrasonic motor. The ultrasonic applicator may be of any shape, including, but not limited to, an elongate solid probe, and elongate hollow probe, a flat radiating plate, or a convex radiating lens. The ultrasonic applicator has a distal surface for engagement with tissues of a patient. The distal surface may, in the preferred embodiment, be shaped to achieve a desired surgical effect, including cutting, fragmentation, boring, and coagulation. The combination of the ultrasonic motor and the ultrasonic applicator are vibratable at a resonant frequency.

A power control circuit is electrically connected to the ultrasonic motor for supplying electrical power to the ultrasonic motor to produce ultrasonic frequency vibratory energy that is applied to the ultrasonic applicator to produce vibratory motion in the ultrasonic applicator.

A vibration monitor circuit is electrically connected to the power control circuit for measuring an electrical vibration signal at the resonant frequency and proportional to a vibratory amplitude of the ultrasonic applicator so that the power control circuit supplies electrical power to the ultrasonic motor at the resonant frequency. The electrical vibration signal may be proportional to a current or a voltage of the electrical power supplied to the ultrasonic motor by the power control circuit or it may be generated by a vibration sensing transducer located in or near the ultrasonic motor.

A profile generator circuit is electrically connected to the power control circuit for producing a profiled pulse signal with a first profile and a maximum magnitude during a first time portion and a second profile and a minimum magnitude during a second time portion. The first time portion is generally the rising portion plus the time at maximum magnitude of the profiled pulse signal and the second time portion is generally the falling portion plus the time at minimum magnitude of the profiled pulse signal. The first profile is the shape of the leading edge of the profiled pulse signal as it ascends from the minimum magnitude to the maximum magnitude. The second profile is the shape of the trailing edge of the profiled pulse signal as it descends from the maximum magnitude to the minimum magnitude. The profiled pulse signal, in combination with the electrical vibration signal, is used in the power control circuit to adjust the supply of electrical power to the ultrasonic motor to produce profiled pulses of ultrasonic frequency vibratory energy.

To best suppress the phenomenon described herein as mode coupling and to achieve maximum vibratory performance the first time portion should be less than fifty milliseconds in duration, but not less than one millisecond in duration to ensure a sufficient surgical effect. The preferred range for the first time portion is between about five milliseconds and about forty milliseconds. The second time portion should be greater than three times the duration of the first time portion. The preferred duration for the second time portion is between about four and ten times the duration of the first time portion. The maximum magnitude should be in the range between two and twenty times the minimum magnitude to achieve an expedient surgical effect. The preferred range for the maximum magnitude is between four and ten times the minimum magnitude.

It is preferred that the rising portion of the first profile and the falling portion of the second profile be monotonically increasing and decreasing shapes, respectively. Monotonically, increasing refers to a shape with a continuous rise with time, without downward dips. Monotonically decreasing refers to a shape with a continuous fall with time, without upward bumps.

The preferred range of resonant frequencies for ultrasonic surgical devices with ultrasonic applicators shaped like elongate probes, either solid or hollow, is between 20 kHz and 80 kHz. The preferred range of resonant frequencies for ultrasonic surgical devices with ultrasonic applicators shaped like a flat radiating plate or a convex radiating lens is between 80 kHz and 200 kHz.

A profiled pulse signal may be generated in any time sequence such that the constraints expressed above are met. However, it has been found that mode coupling is best suppressed if a profiled pulse signal is generated not more than twenty times per second. To minimize the effective dose of ultrasonic vibratory energy applied to the tissues of a patient it is preferred that the profiled pulse signal be generated even less often, for example ten times per second.

The second time portion of the profiled pulse signal may vary between consecutive profiled pulse signals. This has the effect of further reducing mode coupling and the stimulation of parasitic modes of vibration.

The preferred ultrasonic surgical apparatus may have an axis passing through the ultrasonic motor and the ultrasonic applicator. The ultrasonic motor and the ultrasonic applicator are symmetric about the axis along which they are disposed for delivery of ultrasonic frequency vibratory energy in the direction of the axis.

A method of using profiled pulses of ultrasonic frequency vibratory energy to generate an expedient surgical effect and suppress or eliminate mode coupling is disclosed. The method includes the steps of engaging a medium, such as tissues of a patient, with the ultrasonic applicator of the ultrasonic surgical apparatus and powering the ultrasonic surgical apparatus with profiled pulses of ultrasonic frequency vibratory energy, the profiled pulses with a first profile and a maximum magnitude during a first time portion and a second profile and a minimum magnitude during a second time portion, the second time portion greater than three times the duration of the first time portion, the maximum magnitude between two and twenty times the minimum magnitude, and the first time portion between one millisecond and fifty milliseconds in duration.

BRIEF DESCRIPTION OF THE DRAWINGS

The novel features of the invention are set forth in the appended claims. The invention will be best understood by reference to the following figures when read in conjunction with the detailed description of the invention.

FIG. 2 is a waveform diagram illustrating the components of the profiled pulse signal and profiled pulses of ultrasonic frequency vibratory energy.

DETAILED DESCRIPTION OF THE INVENTION

Figure 1:
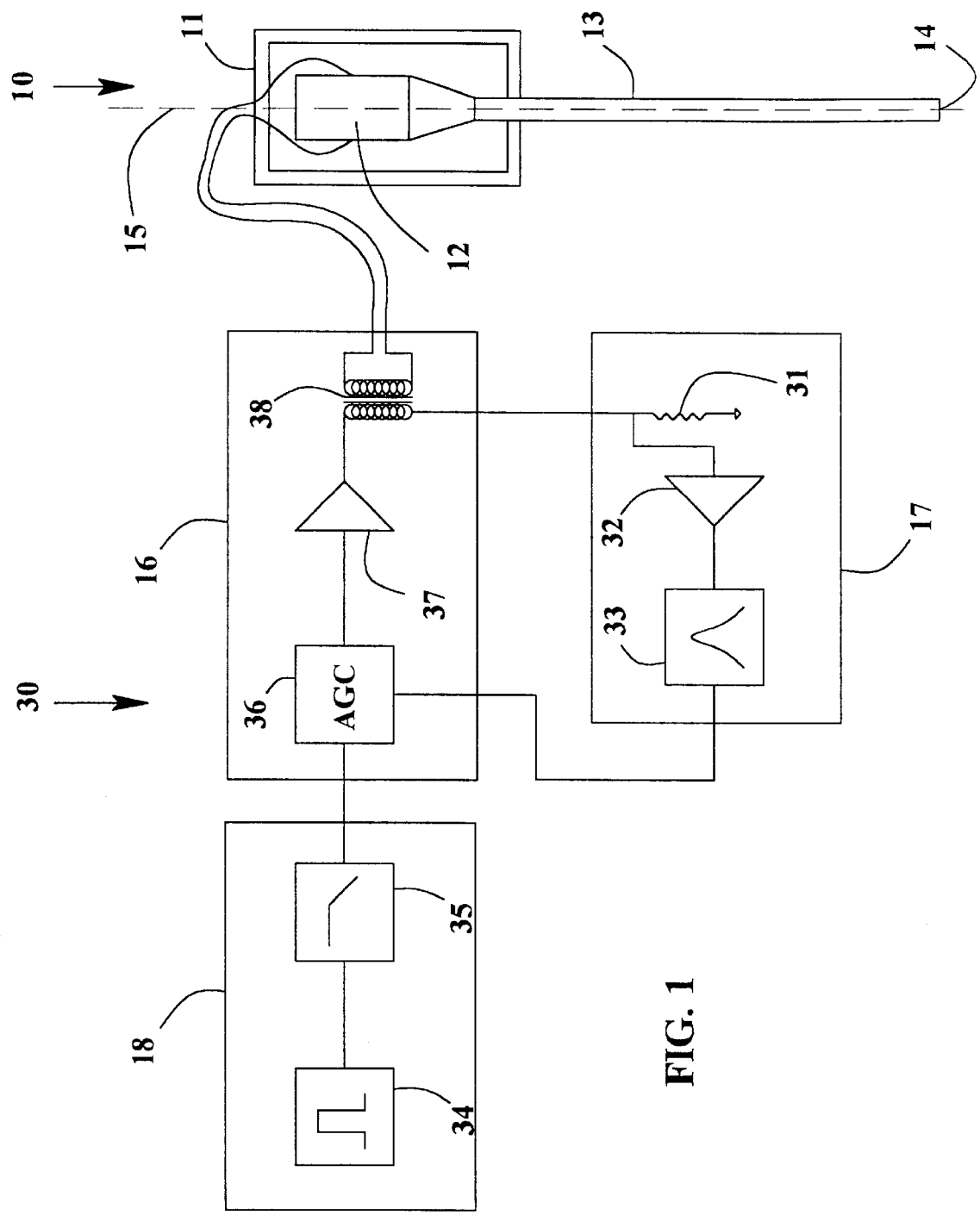
FIG. 1 is a functional block diagram and partial circuit diagram of an ultrasonic surgical apparatus and circuits for delivery of profiled pulses of ultrasonic frequency vibratory energy.
Figure 3A:
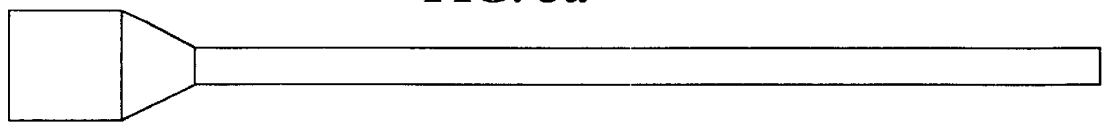
FIG. 3 shows the form of four types of ultrasonic applicators.
Figure 3B:
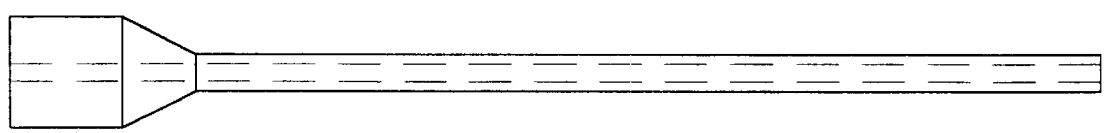
Figure 3C:
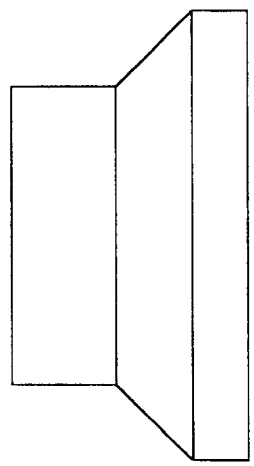
Figure 3D:
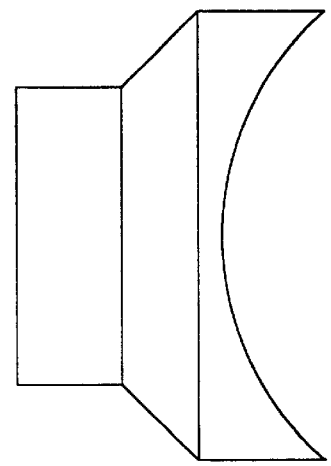

Referring to the drawings, FIG. 1 is a functional block diagram and partial circuit diagram of an ultrasonic surgical apparatus 10 and circuits 30 for delivery of profiled pulses of ultrasonic frequency vibratory energy. The ultrasonic surgical apparatus 10 includes a housing 11 to be held and manipulated by a user, an ultrasonic motor 12 supported within the housing 11, and an ultrasonic applicator 13 connected to the ultrasonic motor 12 and extending beyond the housing 11. In FIG. 1 the ultrasonic applicator 13 depicted is an elongate probe. The housing 11 may be fabricated from metals or plastics, the preferred materials are steam sterilizable plastics such as Delrin (acetal homopolymer) or Radel (polyphenylsulphone). The ultrasonic motor 12 may be constructed from piezoelectric ceramics or magnetostrictive metals. The preferred materials are piezoelectric ceramics such as PZT-4 or PZT-8. The ultrasonic applicator 13 may be fabricated from metal materials such as aluminum, stainless steel, or titanium. The preferred materials for the ultrasonic applicator 13 are titanium or titanium alloys such as Ti6A14V. In combination, the ultrasonic motor 12 and the ultrasonic applicator 13 have a resonant frequency. The resonant frequency is the frequency of preferred longitudinal vibration. The ultrasonic applicator 13 has a distal surface 14 for engagement with tissues of a patient. The distal surface 14 may be shaped to achieve a desired surgical effect. The ultrasonic motor 12 and the ultrasonic applicator 13 may be disposed along and are symmetric about an axis 15.

A power control circuit 16 is electrically connected to the ultrasonic motor 12 for supplying electrical power to the ultrasonic motor 12 to produce ultrasonic frequency vibratory energy that is applied to the ultrasonic applicator 13 to produce vibratory motion in the ultrasonic applicator 13. An automatic gain control element 36 receives an electrical vibration signal from a vibratory monitor circuit 17 and a profiled pulse signal from a profile generator circuit 18. The automatic gain control element 36 adjusts the input to a power amplifier 37 so that electrical power is supplied to the ultrasonic motor 12 through an output transformer 38 at the resonant frequency to produce profiled pulses of ultrasonic frequency vibratory energy. A preferred embodiment of the circuit elements of the automatic gain control element 36 is shown in the application notes for the Analog Devices 633, an integrated circuit multiplier, 1992 Analog Devices Special Linear Reference Manual, pages 2–52,53. In an alternative embodiment, the automatic gain control element 36 may be replaced with an automatic phase control element that includes a phase-locked-loop circuit that maintains a selected phase relationship between the electrical vibration signal and a reference signal.

The vibration monitor circuit 17 is electrically connected to the power control circuit 16 for measuring an electrical vibration signal at the resonant frequency and proportional to a vibratory amplitude of the ultrasonic applicator 13. The preferred electrical vibration signal is proportional to a current of the electrical power supplied by the power control circuit 16. A current sense resistor 31 may be located in-line with the primary of the output transformer 38. The voltage across the current sense resistor 31 is applied to and amplified by a signal amplifier 32 and the output of the signal amplifier 32 is applied to a band-pass filter 33. The output of the band-pass filter 33 is the electrical vibration signal that is in electrical communication with the power control circuit 16.

The profile generator circuit 18 is electrically connected to the power control circuit 16 for producing a profiled pulse signal. A digital pulse generator 34 generates a pulse signal that is applied to a low-pass filter 35. The low-pass filter 35 profiles the leading and trailing edges of the pulse signal generated by the digital pulse generator 34. The output of the low-pass filter 35 is the profiled pulse signal that is in electrical communication with the power control circuit 16.

A detailed waveform diagram illustrating the components of the profiled pulse signal and profiled pulses of ultrasonic frequency vibratory energy is shown in FIG. 2. FIG. 2a shows the output of the digital pulse generator 34, with a maximum magnitude 20 during a first time portion 21 and a minimum magnitude 22 during a second time portion 23. To best suppress mode coupling the first time portion 21 should be in the range between one millisecond and fifty milliseconds, and the second time portion 23 should be greater than three times the duration of the first time portion 21. The preferred duration for the first time portion 21 is between five milliseconds and forty milliseconds. For example, if the first time portion 21 is ten milliseconds then the second time portion 23 must be greater than thirty milliseconds in duration, preferably greater than forty milliseconds. The maximum magnitude 20 should be in the range between two and twenty times the minimum magnitude 22. The preferred range for the maximum magnitude is between four and ten times the minimum magnitude 22. For example, if the minimum magnitude 22 has a value of two then the maximum magnitude must be between four and forty, preferably between eight and twenty.

FIG. 2b shows the profiled pulse signal, a result of the application of the output of the digital pulse generator 34 to the low-pass filter 35. The profiled pulse signal has a monotonically increasing shape 24 and a maximum magnitude 20 and a monotonically decreasing shape 25 and a minimum magnitude 22.

FIG. 2c shows profiled pulses of ultrasonic frequency vibratory energy that correspond to application of the profiled pulse signal, in combination with the electrical vibration signal, to the power control circuit 16.

The profiled pulse signal may be generated as a single event or it may be repeated. To best suppress mode coupling and minimize heating in the ultrasonic motor and the ultrasonic applicator the repetition rate should be less than twenty times per second. The preferred repetition rate is in the range between four and ten times per second.

FIG. 3 shows four examples of ultrasonic applicators. The ultrasonic applicator may be an elongate solid probe as shown in FIG. 3a, an elongate hollow probe as shown in FIG. 3b, a flat radiating plate as shown in FIG. 3c, or a convex radiating lens as shown in FIG. 3d.

Ultrasonic surgical devices typically operate at frequencies between 20 kHz and 80 kHz, most specifically when the ultrasonic applicator is shaped like an elongate solid or hollow probe. When the ultrasonic applicator is shaped like a flat radiating plate or a convex radiating lens the operating frequency may be higher, from 80 kHz up to about 200 kHz.

What is claimed is:

1. A method for surgically affecting tissue in an animal by applying ultrasonic frequency vibratory energy comprising:
   applying a first profile of a pulse of ultrasonic frequency vibratory energy said first profile having a maximum amplitude during a first time portion;
   applying a second profile of a pulse of ultrasonic frequency vibratory energy said second profile having a minimum amplitude during a second time portion wherein;

the first time portion is between one millisecond and fifty milliseconds in duration;

the second time portion is at least three times greater than the first time portion; and the maximum amplitude is in the range between two to twenty times the minimum amplitude;

and repeating the application of said first and second profiles of a pulse of ultrasonic frequency vibratory energy.

2. The method of claim 1 wherein said second time portion is between four and ten times the duration of the first time portion.

3. The method of claim 1 wherein the first profile is monotonically increasing and the second profile is monotonically decreasing.

4. The method of claim 1 wherein said pulse has a shape substantially as shown in FIG. 2c.

5. The method of claim 1 wherein said pulse is generated no more than twenty times per second.

6. The method of claim 5 wherein said pulse is generated no more than ten times per second.

* * * * *